Jan. 19, 1965 C. G. DUEHRSEN Plant Pat. 2,466
ROSE PLANT
Filed Nov. 18, 1963
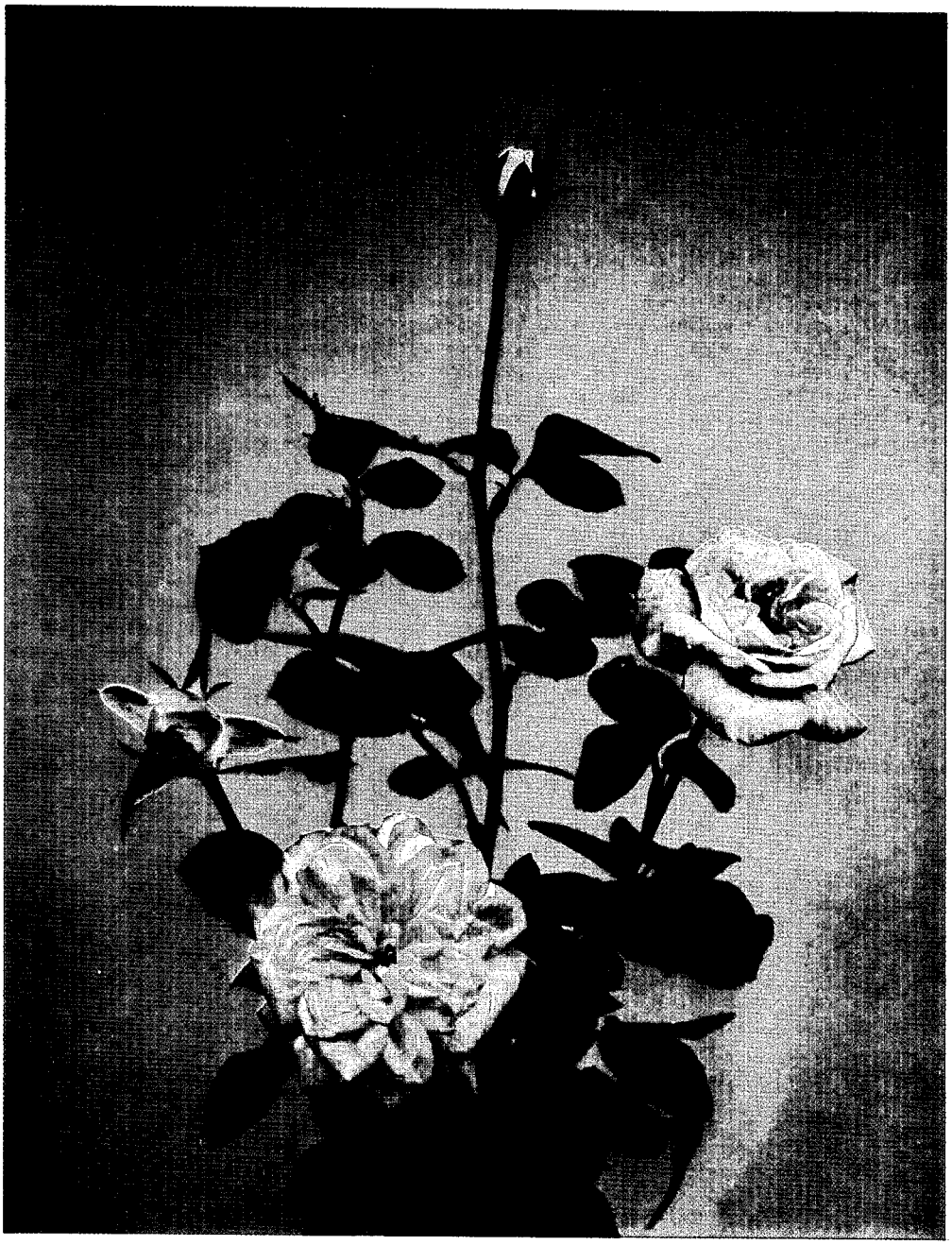
Inventor.
Carl G. Duehrsen
By: Robb & Robb
Attorneys.

United States Patent Office

Plant Pat. 2,466
Patented Jan. 19, 1965

2,466
ROSE PLANT

Carl G. Duehrsen, Montebello, Calif., assignor to Constance A. Elmer, La Quinta, Calif.

Filed Nov. 18, 1963, Ser. No. 324,903
1 Claim. (Cl. Plt.—22)

The present invention relates to a new and distinct variety of rose plant of the floribunda class, which was originated by me as a selected seedling derived from crossing the variety "Oriental Charm" (Plant Patent No. 2,106) with the variety "Circus" (Plant Patent No. 1,382). As the result of this breeding, I have produced a new and improved rose variety which is endowed with the following unique combination of outstanding characteristics which distinguish the new variety from its parents, as well as from all other varieties of which I am aware:

(1) Prolific flower production and exceptionally good blooming habits;

(2) Attractive, lustrous, shiny green foliage with red veins which well clothes the plant and presents a very neat apppearance at all times;

(3) Good resistance to mildew and blackspot;

(4) Attractive and distinctive clear bronze red new growth;

(5) A distinctive, attractive, full and clear flower color ranging from Moderate Reddish Orange in the bud stage through Strong Reddish Orange in the open flower stage, which ages to an attractive Moderate Reddish Brown, said flowers being borne on reddish stems;

(6) A flower habit of dropping cleanly;

(7) A rare, exotic, very sweet fragrance of the flowers which is usually lacking in floribunda roses; and (8) Exceptionally good keeping qualities of the flowers both on the bush and as cut flowers.

Asexual reproduction of my new variety by budding, as performed by me at Montebello, California, and also as performed at Chino, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Munsell Color Chart, published by Munsell Publishing Company of Baltimore, Maryland, except where general color terms of ordinary significance are obvious.

Type: Hardy; seedling; for cut flowers and for garden decoration.
Class: Floribunda.
Breeding: Seedling.
*Seed parent.*—"Oriental Charm."
*Pollen parent.*—"Circus."
Propagation: Holds its distinguishing characteristics through succeeding propagations by budding.

*Flower*

Locality where grown and observed: Chino, California.
Continuity: Continuous.
Fragrance: Strong. Nature—exotic perfume; very sweet.
Flowers borne: Both singly and several to stem; in clusters; on strong stems ranging from short to long length.
Quantity of bloom: Free and abundant; both outdoors and in greenhouse.
Bud:
*Peduncle.*—Medium length; slender; erect; almost smooth; with few red prickles. Color—Reddish green.
*Before Calyx breaks.*—Size—medium. Form—oval; with foliaceous appendages on the surface of the bud with much cut bristle-like foliaceous parts extending beyond the tip of the bud equal to ½ of its length. Color—bronze green.
*As calyx breaks.*—Color—Orange Red, Plate 7.5R 3/6.
*As first petal opens.*—Size—medium. Form—ovoid; long sepals. Color: outside—from Orange Red, Plate 7.5R 5/13 to Gold, Plate 5Y 9/9 were overlapped; inside—Orange Red, Plate 7.5R 5/13.
*Opening.*—Opens up well.
Bloom:
*Size (when fully open).*—Large for its class; from 3½ inches to 4½ inches in diameter.
*Petalage.*—Very double (many petals, usually with no stamens showing); from 60 to 70 petals, arranged irregularly.
*Form.*—Full at first, but becoming open; petals being rolled outward.
Petals:
*Texture.*—Thick.
*Appearance.* — Inside — satiny. Outside — satiny-velvety.
*Shape.*—Outside—oval. Intermediate—oval. Inside—lanceolate.

This description of a newly opened flower was made from a rose grown outdoors during the month of April at Montebello, California:

*Color.*—Outer petal: outside surface—Moderate Reddish Brown, Plate 7.5R 3/6; inside surface—Strong Reddish Orange, Plate 7.5R 5/13. Intermediate petal: outside surface—Yellow, Plate 5Y 9/9; inside surface—Reddish Orange, Plate 7.5R 5/13. Inner petal: outside surface—slightly lighter than Yellow, Plate 5Y 9/9; inside surface—slightly lighter than Reddish Orange, Plate 7.5R 5/13.

This description was made from a rose that was open for three days outdoors during the month of April at Montebello, California:

*Color.*—Outer petal: outside surface—Moderate Reddish Brown, Plate 7.5R 3/6; inside surface—Strong Reddish Orange, Plate 7.5R 5/13, with gold at base. Inner petal: outside surface—somewhat lighter than Moderate Reddish Brown, Plate 7.5R 3/6; inside surface—somewhat lighter than Strong Reddish Orange, Plate 7.5R 5/13, with gold at base.
*General color effect.*—Newly opened flower—Strong Reddish Orange, Plate 7.5R 5/13. Three days open—deepens in color to Moderate Reddish Brown, Plate 7.5R 3/6.
*Behavior.*—Drop off cleanly; deepening to brown red.
*Flower longevity.*—On bush in garden—5 days or even longer at all times. Cut roses grown outdoors and kept at living room temperatures—5 or 6 days at all times.

*Reproductive Organs*

Stamens: Very few; irregularly arranged about pistils; mixed with petaloids. Color—golden.
Filaments: Few; short. Color—yellow.
Anthers: Small; open at various times. Color—yellow.
Pollen: Sparse. Color—lemon.
Pistils: Very few.
Styles: Very uneven; short; loosely bunched.

Stigma: Color—yellow.

Hips: Globular; smooth; do not mature or ripen, but fall off while green, if they form at all. Color—green.

Sepals: Falling soon; long; spear-shaped; re-curved. Color—bronze green on outside and pubescent on inside.

*Plant*

Foliage:

*Leaves.*—Compound of 3, 5 and 7 leaflets; abundant quantity; medium size; leathery; glossy.

*Leaflets.*—Shape—oval. Margin—simply serrate.

*Color.*—Mature: upper surface—dark green; under surface—grey green. Young: upper surface—very bronze red. under surface—light bronze red.

*Rachis (the supporting stem of the compound leaf).*—Light. Upper side—smooth; grooved. Under side—sparsely thorny (about 2 thorns to each).

*Stipules.*—Moderately short; with short points turning out at an angle of less than 45°.

*Disease resistance.*—Very good resistance to mildew and blackspot, as determined by comparison with other varieties grown under comparable cultural conditions at Montebello and Chino, California.

Growth:

*Habit.*—Bushy; upright, full.

*Growth.*—Vigorous.

*Canes.*—Medium caliper.

*Main stems.*—Color—green bronze. Thorns—few; medium length; straight. Prickles — none. Hairs—none.

*Branches.* — Color — green bronze. Thorns—few; short; straight. Prickles—none. Hairs—none.

*New shoots.*—Color—bronze red. Thorns—very few; short; straight; narrow. Prickles—none. Hairs—none.

I claim:

A new and distinct variety of rose plant of the floribunda class, substantially as herein shown and described, characterized particularly as to novelty by the unique combination of a prolific flowering habit and an exceptionally good blooming habit, attractive, lustrous, shiny green foliage with red veins which well clothe the plant and present a very neat appearance at all times, good resistance to mildew and blackspot, attractive and distinctive clear bronze red new growth, a distinctive, attractive, full and clear flower color ranging from Moderate Reddish Orange in the bud stage through Strong Reddish Orange in the open flower stage which ages to an attractive Moderate Reddish Brown, said flowers being borne on reddish stems, a flower habit of dropping cleanly, a rare, exotic, very sweet flower fragrance, and exceptionally good keeping qualities of the flowers both on the bush and as cut flowers.

No references cited.

ABRAHAM G. STONE, *Primary Examiner.*